(12) United States Patent
Zeller

(10) Patent No.: US 7,140,264 B2
(45) Date of Patent: Nov. 28, 2006

(54) SAMPLER AND METHOD OF DISPENSING AND COOLING A FLUID

(75) Inventor: Robert Zeller, Kempten (DE)

(73) Assignee: Endress + Hauser Wetzer GmbH + Co. KG, Nesselwang (DE)

( * ) Notice: Subject to any disclaimer, the term of this patent is extended or adjusted under 35 U.S.C. 154(b) by 0 days.

(21) Appl. No.: 10/926,159

(22) Filed: Aug. 25, 2004

(65) Prior Publication Data

US 2005/0016299 A1   Jan. 27, 2005

(51) Int. Cl.
  *G01N 1/00*   (2006.01)
(52) U.S. Cl. .................................. 73/863.11
(58) Field of Classification Search ............. 73/863.11, 73/863.12, 864.34, 864.35, 864.73
  See application file for complete search history.

(56) References Cited

U.S. PATENT DOCUMENTS

| 1,798,032 A | 3/1931 | Rice |
| 2,348,806 A * | 5/1944 | Gillard et al. ........... 73/863.11 |
| 3,795,347 A * | 3/1974 | Singer ...................... 73/864.35 |
| 3,880,011 A | 4/1975 | Johnson |
| 3,897,687 A | 8/1975 | Burberry |
| 4,077,263 A | 3/1978 | Brailsford |
| 4,195,524 A | 4/1980 | Hansen |
| 4,283,948 A | 8/1981 | Longsworth |
| 4,357,836 A | 11/1982 | Kokesh |
| 4,485,684 A | 12/1984 | Weber et al. |
| 4,628,748 A * | 12/1986 | Jogan et al. ............. 73/863.01 |
| 5,587,926 A | 12/1996 | Chiu et al. |

* cited by examiner

*Primary Examiner*—Robert Raevis
(74) *Attorney, Agent, or Firm*—Bacon & Thomas

(57) ABSTRACT

The sampler comprises a vessel assembly for taking, conducting, and storing a fluid sample to be stored at a predeterminable storage temperature as well as a cooling assembly, thermally coupled to the vessel assembly, for cooling the fluid sample. The cooling assembly has a first cooling volume, which encompasses the vessel assembly, and a second cooling volume, which jackets the vessel assembly. To cool the fluid sample, the internal temperature of the vessel assembly is lowered by means of the cooling assembly prior to and/or during the dispensing of the fluid sample, and the fluid is subsequently conducted or held in the vessel assembly.

35 Claims, 3 Drawing Sheets

SAMPLER AND METHOD OF DISPENSING AND COOLING A FLUID

FIELD OF THE INVENTION

Figure 1:
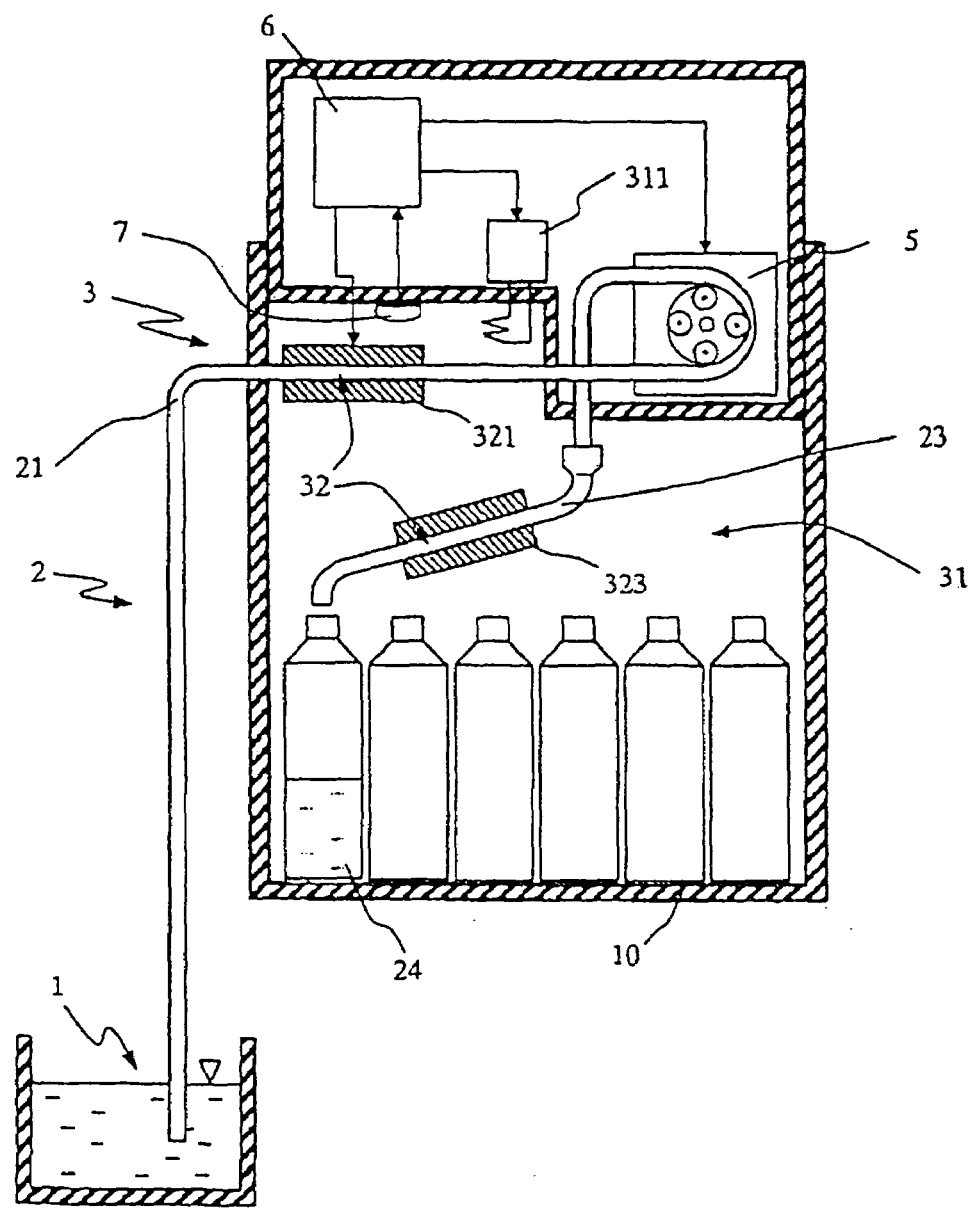

This invention relates to a sampler and to a method of dispensing and cooling a fluid.

BACKGROUND OF THE INVENTION

Fluids of different origins and applications often have to be monitored for their chemobiological condition, which is determined, among other things, by substances being entrained in the fluid. To monitor aqueous fluids, particularly in drinking water treatment or wastewater purification plants, representative fluid samples have to be taken at sampling locations in a spatial and temporal distribution, and examined. The volume of such fluid samples generally ranges between approximately 10 ml and 500 ml.

The samples are commonly taken and dispensed by means of a sampler. U.S. Pat. Nos. 3,795,347, 3,880,011, 4,415,011, and 5,587,926, for example, disclose a sampler for dispensing a sample of a fluid withdrawn at a sampling location, said sampler comprising:
 a vessel assembly
  with a tubular intake vessel for conducting a moving fluid, and
  with a storage vessel for storing the fluid sample.

Samplers of the kind described generally include a suitable pumping device, particularly a pumping device controlled by control electronics, by means of which the fluid is caused to flow into the vessel assembly. In many cases, a vacuum pump or a displacement pump, particularly a peristaltic pump acting mechanically on the intake vessel, is used, as described, for example, in U.S. Pat. Nos. 3,880,011, 4,077,263, 4,660,607, or 5,587,926.

Furthermore, the vessel assembly of the sampler may include a metering vessel for metering a volume of the fluid sample.

Moreover, the sampler commonly comprises a single cabinet in which the vessel assembly, the pumping device, and electronic units may be mounted.

Because of the entrained substances, particularly because of bacteria, but also because of particular chemical compounds, metabolic processes take place in the fluid, which constantly change the chemobiological condition of the fluid. The change in the chemobiological condition of the fluid per unit time is commonly referred to as the activity of the fluid. The activity is temperature-dependent and increases with increasing fluid temperature and particularly also with an increasing temperature of the fluid sample.

The quality of the monitoring is determined, inter alia, by how closely the chemobiological condition of the fluid sample at the time of examination corresponds with the chemobiological condition of the fluid at the sampling instant. In many cases, however, considerable time elapses between the sampling and the examination of the sample. Therefore, the fluid samples are metered and stored in suitable storage vessels, e.g., in sample bottles.

If the fluid sample is to represent the chemobiological condition existing in the fluid at the sampling instant as precisely as possible, the activity of the fluid sample, averaged over the period between sampling and examination, must be minimized. Therefore, as shown in U.S. Pat. No. 5,587,926 or in WO-A 90 14 586, for example, the fluid samples are usually cooled to a constant storage temperature of, e.g., 4° C. (=277 K), at which a permissible activity is not exceeded.

To cool the fluid samples, the storage vessels are stored at an appropriate temperature in a cold-storage room, which, as proposed in U.S. Pat. No. 5,587,926, for example, may be provided directly in the sampler cabinet, and the fluid samples taken by the sampler are dispensed from the sampling location practically directly into the storage vessels, where they are cooled.

It has turned out, however, that with this method, the cooling rates, particularly at a fluid temperature at the sampling location of above 15° C., may be too low, so that the activity of the fluid sample until the time of examination may be too great. For example, at a fluid temperature of 16° C. and for a volume of the fluid sample of 500 ml, an average cooling rate of 1 K/h, and thus a cooling time until attainment of the storage temperature of 12 h, was measured. Because of the excessive activity of the fluid sample, during the dispensing and cooling, the chemobiological condition of the fluid sample may change considerably from the chemobiological condition at the sampling instant.

SUMMARY OF THE INVENTION

It is therefore an object of the invention to provide a sampler for dispensing and cooling such a fluid sample with which the cooling time, and thus the activity of the fluid sample, can be reduced.

A further object of the invention is to provide a method of dispensing and cooling such a fluid sample whereby the cooling time is reduced.

To attain the first-mentioned object, the invention provides a sampler for dispensing and cooling a sample, to be stored at a predeterminable storage temperature, of a fluid withdrawn at a sampling location and having an instantaneous sampling temperature greater than the storage temperature, said sampler comprising:
 a vessel assembly of a predeterminable volume with
  an internal temperature averaged over the volume,
  a tubular intake vessel for conducting the withdrawn fluid, and
 a storage vessel for storing the fluid sample; and
 a cooling assembly, thermally coupled to the vessel assembly, for setting the internal temperature of the vessel assembly and comprising
  a first cooling volume, encompassing at least the storage vessel and having a predeterminable first cooling temperature, for cooling the fluid sample to the storage temperature, and
  a second cooling volume, jacketing the vessel assembly at least in sections and having a predeterminable second cooling temperature, for cooling the withdrawn fluid sample to a temperature below the sampling temperature.

Furthermore, the invention consists in a method of dispensing and cooling a sample, to be stored at a predeterminable storage temperature, of a fluid withdrawn at a sampling location and having an instantaneous sampling temperature greater than the storage temperature, by means of a sampler comprising:
 a vessel assembly of a predeterminable volume with
  an internal temperature averaged over the volume,
  a tubular intake vessel for conducting the withdrawn fluid, and a storage vessel for storing the fluid sample; and a cooling assembly, thermally coupled to the vessel assembly, for setting the internal temperature of the vessel assembly and comprising a first cooling volume, encompassing at least the storage vessel and having a predeterminable first cooling temperature, for cooling the fluid sample to the storage temperature, the internal temperature of the vessel assembly prior to the dispensing, an initial internal temperature of the vessel assembly, being lower than the sampling temperature, the first cooling temperature being set at the storage temperature after the storing of the fluid sample, said method comprising the steps of:

lowering the internal temperature of the vessel assembly by means of the cooling assembly to a temperature lower than the initial internal temperature of the vessel assembly;

letting the withdrawn fluid flow through the intake vessel; and letting a partial volume of the withdrawn fluid, which serves as the fluid sample, flow into the storage vessel.

In a first embodiment of the sampler according to the invention, the second cooling volume is encompassed at least in part by the first cooling volume.

In a second embodiment of the sampler according to the invention, the vessel assembly comprises a metering vessel closable temporarily at the outlet end for metering the fluid sample.

In a third embodiment of the sampler according to the invention, the vessel assembly comprises a distributing vessel for dispensing the fluid sample into the storage vessel.

In a fourth embodiment of the sampler according to the invention, the cooling assembly comprises a first cooling element, disposed at the intake vessel, for setting an internal temperature of the intake vessel.

In a fifth embodiment of the sampler according to the invention, the the cooling assembly comprises a second cooling element, disposed at the metering vessel, for setting an internal temperature of the metering vessel.

In a sixth embodiment of the sampler according to the invention, the cooling assembly comprises a third cooling element, disposed at the distributing vessel, for setting an internal temperature of the storage assembly.

In a seventh embodiment of the sampler according to the invention, the cooling assembly comprises a fourth cooling element, disposed at the storage vessel, for setting the internal temperature of the storage vessel.

In an eighth embodiment of the sampler according to the invention, the first cooling element is flow cooler.

In a ninth embodiment of the sampler according to the invention, the metering vessel is disposed within the first cooling volume.

In a tenth embodiment of the sampler according to the invention, the metering vessel is partially encompassed by the first cooling volume.

In an eleventh embodiment of the sampler according to the invention, the fluid is drinking water or wastewater.

In a first embodiment of the method according to the invention, the internal temperature of the vessel assembly is set at the lower temperature by lowering the first cooling temperature temporarily to a first temperature below the storage temperature.

In a second embodiment of the method according to the invention, a cooling assembly with a second cooling volume encompassing the vessel assembly at least in sections and having a predeterminable second cooling temperature is used to cool the withdrawn fluid to a temperature below the sampling temperature, and, before fluid is allowed to flow into the storage vessel, the lower internal temperature of the vessel assembly is lowered to a second temperature below the storage temperature by temporarily setting the second cooling temperature.

In a third embodiment of the method according to the invention, the fluid sample is taken from a aqueous fluid.

A basic idea of the method according to the invention is to reduce the activity of the withdrawn fluid, and thus of the fluid sample, already during the dispensing process and to reach a required minimum of the activity in the shortest possible time. This is achieved in the invention by cooling a fluid-conducting volume of the vessel assembly prior to the dispensing process by means of a suitable cooling assembly. This coolable volume may extend over the total internal volume of the vessel assembly, so that the cooling of the fluid begins immediately upon its entry into the vessel assembly, or comprise only part of the total internal volume.

One advantage of the invention is that the activity of the fluid sample can be reduced very quickly, particularly also at higher fluid temperatures at the sampling location. Another advantage of the method is that it can also be applied to existing vessel assemblies.

DETAILED DESCRIPTION OF THE PREFERED EMBODIMENTS

While the invention is susceptible to various modifications and alternative forms, exemplary embodiments thereof have been shown by way of example in the drawings and will be described in detail. It should be understood, however, that there is no intent to limit the invention to the particular forms disclosed, but on the contrary, the intention is to cover all modifications, equivalents, and alternatives falling within the spirit and scope of the invention as defined by appended claims.

The invention and further advantages will now be explained in more detail with reference to the accompanying drawings, which show embodiments of the invention.

Figure 2:
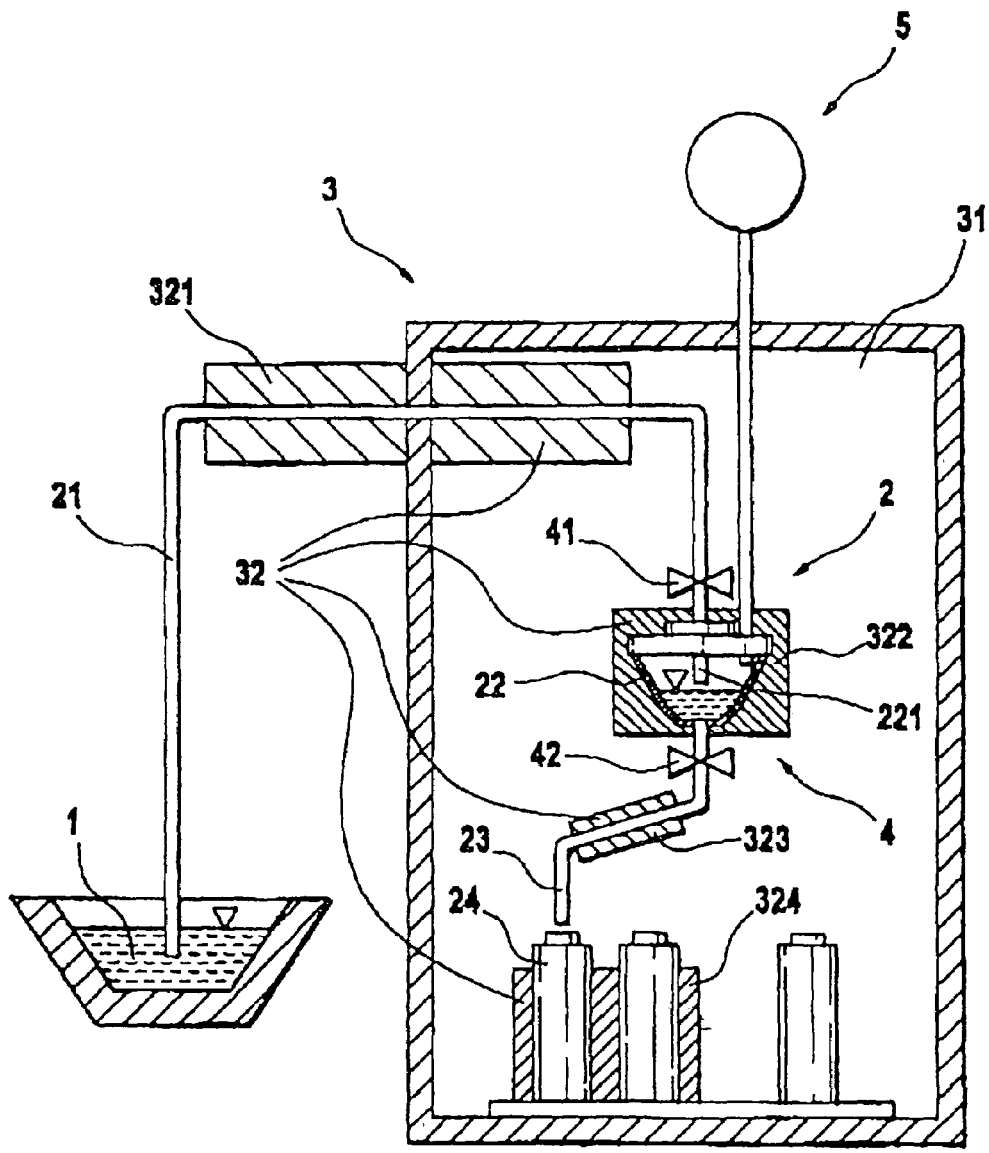

FIG. 1 schematically shows a first embodiment of a sampler;

FIG. 2 schematically shows a second embodiment of a sampler; and

Figure 3:
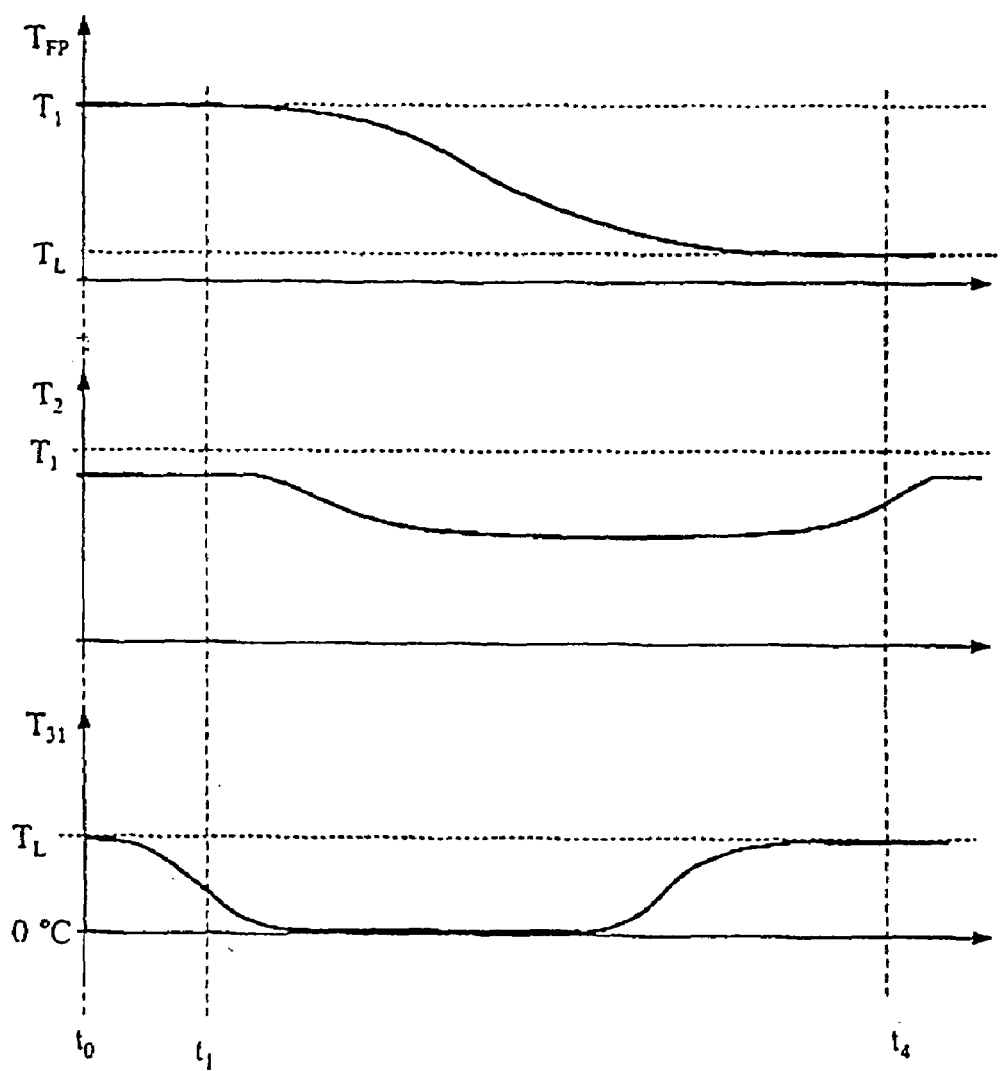

FIG. 3 shows temperature-time characteristics in the sampler of FIG. 1 or 2, which are set using the method of the invention.

FIGS. 1 and 2 each show schematically a sampler for withdrawing a fluid, particularly an aqueous fluid, at a sampling location 1 and for metering, dispensing, and storing a sample of the fluid. The sampler comprises a vessel assembly 2 of a predeterminable volume which serves to conduct the withdrawn fluid and hold the fluid sample, and which is disposed, at least in part, in a cabinet 10, particularly in a single cabinet.

The sampler may be both a stationary sampler and a transportable sampler.

Vessel assembly 2 comprises at least one intake vessel 21 for withdrawing and conducting the fluid and, at least during operation, a storage vessel 24 for storing the fluid sample.

Intake vessel 21 is tubular in shape and has an inlet-side first end and an outlet-side second end. Preferably, intake vessel 21 is implemented, at least in sections, as a flexible tube, particularly a tube of elastic material. The materials commonly used for such intake vessels in samplers, such as polyethylene and, if necessary, glass, can be used.

In a preferred embodiment of the invention, vessel assembly 2 further comprises a distributing vessel 23 for dispensing the metered fluid sample into storage vessel 24.

Distributing vessel 23, like intake vessel 21, is tubular in shape, and preferably elastically deformable in sections. It is shaped and dimensioned so that a fluid flowing through its outlet-side end can be dispensed into storage vessel 24 through an inlet opening of the latter.

If distributing vessel 23 has only a single outlet-side end as shown in FIGS. 1 and 2, but several fluid samples are to be dispensed in succession, distributing vessel 23 is preferably arranged to swivel such that a fluid flowing through the second end can be dispensed into further storage vessels, which are spatially separated from storage vessel 24. Distributing vessel 23 may also have two or more outlet-side ends and be so designed that if two or more storage vessels have to be filled, each of them is assigned one of the outlet-side ends so that the fluid flowing through the ends can be dispensed into the respective storage vessel.

If distributing vessel 23 is connected directly to intake vessel 21, it may also be implemented by an end-side section of distributing vessel 21 which can be swiveled in a suitable manner to the respective storage vessel to be filled, as is proposed in U.S. Pat. No. 4,415,011, for example.

In a further preferred embodiment of the invention, vessel assembly 2, as shown in FIG. 2, comprises a metering vessel 22 for receiving a partial volume of the fluid and for metering the fluid sample from the partial volume. For this purpose, intake vessel 21 has its second end connected to a first inlet/outlet opening of metering vessel 22, which is preferably located at a highest point of metering vessel 22 or in the vicinity thereof; if necessary, the inlet/outlet opening may also be located at a lower point of metering vessel 22, for example.

Metering vessel 22, as is usual with such metering vessels, has a tubular inlet/outlet piece 221 of predeterminable length, which starts at the inlet/outlet opening and one end of which extends into the volume of the metering vessel. If the predeterminable length of inlet/outlet piece 221 is not variable during operation of the sampler, the inlet/outlet piece will advantageously be implemented by an outlet-side section of intake vessel 21 which extends perpendicularly from above into the volume of metering vessel 22.

Metering vessel 22 is preferably made of glass; it may also be of any of the other materials commonly used for such metering vessels, such as polyethylene.

In this embodiment of the invention shown in FIG. 2, distributing vessel 23 has an inlet-side first end connected to a temporarily closable outlet opening of metering vessel 22. The outlet opening is preferably located at a lowest point of metering vessel 22; if necessary, it may also be at any other point of metering vessel 22.

As shown in FIG. 2, in this embodiment of the invention, the sampler further comprises a shutoff arrangement 4 which serves to temporarily close sections of vessel assembly 2, particularly metering vessel 22, in a pressure-tight manner.

To temporarily close the inlet/outlet opening of metering vessel 22, a first shutoff element 41 of shutoff arrangement 4 is provided at this opening or at intake vessel 21. To temporarily close the outlet opening of metering vessel 22, a second shutoff element 42 of shutoff arrangement 4 is provided at this outlet opening or at distributing vessel 23. Shutoff elements 41, 42 may be conventional manually, electromechanically, or pneumatically operated valves or slide valves, see U.S. Pat. Nos. 3,795,347 or 3,880,011. If a distributing vessel 23 is used which is elastic at least in sections, the shutoff element may also be designed as a pinch clamp, see U.S. Pat. No. 4,077,263.

The fluid to be sampled with the sampler is a fluid, particularly drinking water or wastewater, that is to be tested, at a location remote from sampling location 1, for its chemical and/or biological properties, particularly for entrained substances or bacteria. Such fluids exhibit a temperature-dependent activity which may cause these chemo-biological properties to chance after the sampling. The higher an instantaneous temperature value of the fluid, the greater the activity of the fluid. Accordingly, the higher the temperature $T_{FP}$ of the fluid sample, the greater the activity of the sample. Therefore, the fluid, after being withdrawn at an instantaneous temperature $T_1$, is stored at a predeterminable low storage temperature $T_L$, particularly at a constant temperature. This storage temperature $T_L$ is chosen so that the resulting activity is reduced to the point where it does not change the fluid sample in an undue manner.

As a rule, the fluid is withdrawn at a relatively high temperature $T_1$, e.g., at 288 K (Kelvin), at which the fluid may exhibit a correspondingly great activity. This, in turn, necessitates cooling the fluid sample as rapidly as possible, i.e., a cooling phase $\Delta t_a$ between the beginning of the withdrawal and the attainment of the storage temperature $T_L$ should be minimized.

The sampler therefore comprises a cooling assembly 3, thermally coupled to vessel assembly 2, for cooling the fluid. "Thermally coupled" means that temperature differences temporarily existing between cooling assembly 3 and vessel assembly 2, particularly a volume of vessel assembly 2, can be nearly equalized, particularly with a slight delay and nearly completely.

In operation, cooling assembly 3 encloses a first cooling volume 31, which has a predeterminable, spatially averaged first cooling temperature $T_{31}$ and encompasses at least storage vessel 24. Cooling volume 31 is formed by the volume of a cold-storage room, as shown in FIGS. 1 and 2. The cold-storage room is preferably provided directly in cabinet 10, and can thus be designed as a transportable cooltainer or as a stationary cooling chamber.

Cooling volume 31 is surrounded by an outer enclosure, particularly by a double-walled enclosure. The enclosure serves both to thermally insulate the cooling volume and, as part of cabinet 10, to provide a supporting structure for vessel assembly 2. It is therefore preferably made, on the one hand, of thermally insulating material, such as polyurethane foam, and, on the other hand, of mechanically strong construction material, such as high-grade steel or polyethylene.

As shown in FIG. 2, cooling volume 31 may be so designed as to also encompass metering vessel 22, if present, and/or part of intake vessel 21. Furthermore, cooling volume 31 is preferably designed in such a way that besides storage vessel 24, further storage vessels can be simultaneously accommodated therein.

At the beginning of a withdrawal of fluid, the first end of intake vessel 21 is connected with sampling location 1, for example by being immersed in the fluid, so as to communicate therewith, as shown in FIGS. 1 and 2. Sampling location 1 may be located in any suitable partial volume of the fluid to be sampled.

At a first instant $t_1$, the fluid is caused to flow into intake vessel 21, which communicates with sampling location 1, and carried onward therein so that, if vessel assembly 2 comprises metering vessel 22, which is connected to intake vessel 22, the fluid reaches the metering vessel at a second instant $t_2$.

As shown schematically in FIGS. 1 and 2, the withdrawal of fluid is accomplished by immersing intake vessel 21 in the fluid being conducted in, e.g., an open channel, and by drawing fluid off against the force of gravity; however, the fluid may also be drawn off from a suitable sampling location 1 in the direction of the force of gravity, or from a pipe or tank.

To withdraw the fluid from sampling location 1, therefore, samplers of the kind described have a pressure source 5, which is connected to vessel assembly 2 and serves to generate a static pressure of predeterminable magnitude in a volume of vessel assembly 2, particularly in the volume of intake vessel 21 and of metering vessel 22, if present, see also U.S. Pat. Nos. 3,795,347, 3,880,011, 4,077,263, or 5,587,926. Accordingly, pressure source 5 may, for instance, be a vacuum pump, particularly a diaphragm or piston pump, or a displacement pump, particularly a peristaltic pump. Since in vessel assemblies of this kind with a pressure source 5 in the form of a vacuum pump, there are virtually no moving parts that are in direct contact with the fluid, such vessel assemblies are generally almost nonwearing, and thus require little maintenance. By contrast, such vessel assemblies with a pressure source 5 in the form a displacement pump are subject to higher mechanical loading and thus require more maintenance, but such a vessel assembly is simpler in construction and, consequently, less expensive.

To withdraw the fluid, a first pressure difference is generated in the volume between the inlet-side and outlet-side ends of intake vessel 21 to draw the fluid into intake vessel 21.

To accomplish this in the sampler according to the embodiment of FIG. 1, intake vessel 21 is set, section by section, into fluid-conveying displacement motions by means of pressure source 5. The fluid sample is then metered by conveying a partial volume beyond a dead volume remaining during this process in intake vessel 21 and transferring it as the fluid sample directly to storage vessel 24, as shown in U.S. Pat. No. 4,660,607, for example.

In the sampler according to the embodiment of FIG. 2, with the inlet/outlet opening open and the outlet opening closed, the static pressure in the volume of metering vessel 22 is first reduced by means of pressure source 5 at least to the point that the fluid flowing against the force of gravity into intake vessel 21 reaches at least a maximum level of intake vessel 21, see also U.S. Pat. No. 4,077,263. The fluid is then allowed to flow into metering vessel 22 until the latter is filled with the partial fluid volume. This partial fluid volume is commonly chosen so that a predeterminable first level above the end of inlet/outlet piece 221 is reached in metering vessel 22. After the partial fluid volume has been filled into metering vessel 22, a second pressure difference is generated in the volume of vessel assembly 2 between the end of inlet/outlet piece 221 and the first end of intake vessel 21, such that part of the partial fluid volume will flow back through inlet/outlet piece 221 into intake vessel 21 and from there to sampling location 1. The flowing back of the fluid continues until a second level reaches the end of inlet/outlet piece 221, so that metering vessel 22 contains only a residual fluid volume, which serves as a fluid sample. The second pressure difference can be generated, for example, by increasing the static pressure in metering vessel 22 by means of pressure source 5 at least to the point that the fluid subsequently flowing against the force of gravity into inlet/outlet piece 221 and into intake vessel 21 reaches at least the maximum level of intake vessel 21. If, as shown in FIG. 2, the end of inlet/outlet piece 221 is at a higher level than a fluid level at sampling location 1, so that a level difference exists between the two, the second pressure difference will preferably be generated by effecting an equalization of the static pressures of sampling location 1 and metering vessel 22. If sampling location 1 is open toward the atmosphere, this can be accomplished by simply supplying metering vessel 22 with air, for example. The resulting pressure difference is then determined essentially by the level difference between the end of inlet/outlet piece 221 and the fluid level. Now that metering vessel 22 holds virtually only the fluid sample, the outlet opening is opened at a third instant $t_3$, and the residual fluid volume is dispensed to storage vessel 24 by means of distributing vessel 23.

After attainment of the essentially constant storage temperature $T_L$ of, e.g., 277 K at an instant $t_4$, the fluid sample in storage vessel 24 is stored. The storage temperature $T_L$ is not higher than a maximum permissible storage temperature of the fluid, but at least equal to a minimum permissible storage temperature of the fluid. If different fluids are contained in cooling volume 31, the maximum permissible storage temperature will be equal to the lowest of the respective maximum permissible storage temperatures of the fluids and the minimum permissible storage temperature will be equal to the highest of the respective minimum permissible storage temperatures.

Analogously, the cooling temperature $T_{31}$ of cooling volume 31, particularly with fluids contained therein, is set to a value not greater than the maximum permissible storage temperature, and thus to a value which is virtually always lower than that of the ambient temperature of cooling volume 31. The cooling temperature $T_{31}$, as is commonly done in such cold-storage rooms, is set by means of an active heat sink 311, such as a heat pump or a Peltier element, which is thermally coupled with the cooling volume. This can be done using any of the temperature control or regulation methods familiar to those skilled in the art.

To implement the control and/or regulation processes necessary for the operation of the sampler, particularly for the withdrawal of fluid and for cooling the fluid sample, the sampler comprises a suitable control circuit 6, which is also housed in cabinet 10. Control circuit 6 is preferably supplied from an external power supply, particularly with an alternating voltage in the 230-V range. Furthermore, particularly if the sampler is transportable as mentioned above, control circuit 6 may also be powered from an on-board supply system of a transport vehicle, from a storage battery which is also mounted in the sampler cabinet, and/or from a solar-cell array. Control circuit 6 may also comprise suitable input/output interfaces, particularly also for manual operation.

In the following, further steps of the method will be explained. During operation of the sampler, an instantaneous internal-temperature distribution with a spatially averaged internal temperature $T_2$ exists in the volume of vessel assembly 2, particularly at and in the walls thereof, at any point in time. Due to heat transfer or heat conduction and due to convection in vessel assembly 2, the value of the internal temperature $T_2$ of the vessel assembly is also dependent on the value of the cooling temperature $T_{31}$.

At an initial instant $t_0$ prior to the withdrawal of fluid, the cooling temperature $T_{31}$ is set at the storage temperature $T_L$ of the fluid, as shown in FIG. 3. Thus, at the intial instant to, there exists an initial internal-temperature distribution with a corresponding average initial internal temperature of the vessel assembly which is lower than the sampling temperature $T_1$.

Since, as shown in FIGS. 1 and 2, cooling volume 31 encompasses only parts of vessel assembly 2, the internal-temperature distribution of the latter, particularly if intake vessel 21 and metering vessel 22 are not or only partially thermally insulated outside cooling volume 31, is influenced correspondingly by an external ambient-temperature distribution.

The further the cooling volume 31 extends over vessel assembly 2 and/or the lower the cooling temperature $T_{31}$, averaged over time cooling phase $\Delta ta$, is set, the smaller a corresponding ratio $T_{2,\Delta ta}/T_L$ of the internal temperature $\Delta ta$ of the vessel assembly, averaged over the cooling phase $\Delta ta$, to the storage temperature $T_L$ will be. The cooling phase $\Delta ta$ follows from the time difference $t_4-t_1$, which lasts from the beginning of the withdrawal of fluid at the instant $t_1$ until the instant $t_4$, at which the fluid sample has reached the storage temperature $T_L$.

The smaller this temperature ratio $T_{2,\Delta ta}/T_L$, the greater a cooling rate of the fluid in vessel assembly 2, also averaged over the cooling phase $\Delta ta$. An increase in the cooling rate shortens the time required for the fluid sample to reach the storage temperature $T_L$, and thus the cooling phase $\Delta ta$.

According to the method of the invention, therefore, prior to the withdrawal of fluid the internal temperature of the vessel assembly is reduced from the initial internal temperature, which is of the order of 1 K to 5 K, for example, to a lower internal temperature, averaged over vessel assembly 2, particularly to a temperature which is lower at the instant $t_1$, see FIG. 3. If necessary, the initial internal temperature of the vessel assembly may also be lowered by more than 5 K.

In a preferred embodiment of the method according to the invention, the cooling temperature $T_{31}$ is temporarily lowered, by means of active heat sink 311, from the storage temperature $T_L$ to a temperature of, e.g., 273 K (=0° C.). This results in a corresponding change in the internal-temperature distribution in vessel assembly 2.

During or after the lowering of the cooling temperature $T_{31}$, the fluid is caused to flow into the vessel assembly 2 in the manner described. Because of the lower internal temperature existing within vessel assembly 2, the fluid sample is cooled to a temperature below the sampling temperature $T_1$. This is effected essentially by heat transfer or by heat conduction in the wall of vessel assembly 2. The cooling of the fluid sample thus begins with its entry into the portion of vessel assembly 2 encompassed by cooling volume 31, and continues, particularly in storage vessel 24, until the fluid sample has taken on the set cooling temperature $T_{31}$. Since, however, the storage temperature $T_L$ to be set for the fluid sample is to be higher than the lowered cooling temperature $T_{31}$, the latter is reraised after a certain time, particularly to the value set at instant $t_0$.

The lowering and reraising of the first cooling temperature $T_{31}$, and thus the cooling of the fluid sample within vessel assembly 2, particularly within storage vessel 24, may be accomplished by use of regulating and/or timing devices. The corresponding regulating and/or control variables can be determined by suitable calibration measurements. The method according to the invention can be implemented in the manner familiar to those skilled in the art using suitable program codes, for example, which are implemented and executed in a microcomputer of control circuit 6. The control signals necessary to carry out the method, e.g., control signals for pressure source 5 or heat sink 311, are provided by control circuit 6 as shown schematically in FIG. 1, and may be generated, for example, by signal output cards controlled by the microcomputer.

During the cooling phase $\Delta ta$, the cooling temperature $T_{31}$, if necessary, may also be set to a value below 273 K. However, the temperature should only be lowered to the point that neither unduly high cooling rates are reached in the fluid nor fluid samples already stored in cooling volume 31 are unduly undercooled. Therefore, the lowering and reraising of the cooling temperature $T_{31}$ must, if necessary, be modified by setting the cooling temperature $T_{31}$ during the cooling phase $\Delta ta$ to intermediate values higher than the lower cooling temperature. The intermediate temperature values can be determined by suitable calibration.

If necessary, particularly if the cooling temperature $T_{31}$ is to be regulated, a suitable measurement signal representative of the cooling temperature $T_{31}$ and/or of the internal temperature of the vessel assembly must be generated in the manner familiar to those skilled in the art. This can be done, for example, using a temperature sensor 7 disposed within cooling volume 31, such as a resistance thermometer or a thermocouple, which is connected, e.g., via a signal input card, to control circuit 6, particularly to the aforementioned microcomputer, see also U.S. Pat. No. 5,587,926.

In a further embodiment of the sampler according to the invention, cooling assembly 3 comprises a second cooling volume 32, which encloses vessel assembly 2 at least in part and has a predeterminable, spatially averaged second cooling temperature $T_{32}$. This second cooling volume 32 is formed at least within sections of the wall of vessel assembly 2 and in the volume of vessel assembly 2 enclosed thereby.

Cooling volume 32 serves, on the one hand, to further extend the coolable volume of vessel assembly 2 in the direction of fluid-sampling location 1. On the other hand, it serves to selectively influence the internal-temperature distribution in vessel assembly 2, and thus to more finely and accurately set the internal temperature $T_2$ of the vessel assembly during the cooling phase $\Delta ta$.

As shown in FIGS. 1 and 2, cooling volume 32 is formed by a first cooling element 321 at intake vessel 21 for setting the internal temperature of the intake vessel, a second cooling element 322 at metering vessel 22 for setting the internal temperature of the metering vessel, a third cooling element 323 at distributing vessel 23 for setting the internal temperature of the distributing vessel, and a fourth cooling element 324 at storage vessel 24 for setting the internal temperature of storage vessel, so that it is divided into corresponding partial cooling volumes. As illustrated in FIG. 1 by the example of cooling element 321, the necessary control signals are also provided by control circuit 6.

For the cooling elements, particularly for cooling element 321, suitable heat pumps can be used. In a preferred embodiment of the invention, cooling element 321 is designed as a flow cooler. It is also possible to use Peltier elements in cooling elements 321, 322, 323, 324.

If necessary, cooling volume 32, as shown in FIG. 1, may also be formed by only three, two, or one of these cooling elements 321, 322, 323, 324, particularly if cooling volume 32 is preferably encompassed at least in part by cooling volume 31, as shown.

The advantage of this embodiment of the invention is that existing samplers can be easily retrofitted with such cooling elements.

In a further embodiment of the method of the invention, prior to the withdrawal of fluid, the internal temperature $T_2$ of the vessel assembly is temporarily lowered by means of one or more of cooling elements 321, 322, 323, 324 to a value of, e.g., 273 K, so that the internal temperature $T_2$ is lower than the initial internal temperature of the vessel assembly, particularly at instant $t_1$.

During or after the lowering of the cooling temperature $T_{32}$, the fluid is again allowed to flow into vessel assembly 2 and thereby cooled to a temperature below the sampling temperature $T_1$. In this embodiment of the invention, the above-described method in which the first cooling temperature $T_{31}$ is lowered may, of course, be used as well.

Prior to the withdrawal of fluid, particularly if two or more successive dispensing operations are performed, fluidic residues are usually removed from vessel assembly 2. This is accomplished in the embodiment of FIG. 2 by generating a static overpressure in the volume of metering vessel 22 and of the connected intake vessel 21 by means of pressure source 5, with the outlet opening of metering vessel 22 closed and the inlet/outlet opening open. Due to this overpressure, residues in intake vessel 21 will be forced out through the first end of the intake vessel. If necessary, by closing the inlet/outlet opening with the outlet opening open, and generating an overpressure in the volume of metering vessel 22, the metering vessel itself and the connected distributing vessel 23 can be freed from fluidic residues; the latter can then be drained through the second end of distributing vessel 23 into a suitable vessel of the sampler or out of the sample. In the embodiment of FIG. 1, fluidic residues can be removed from vessel assembly 2 by simply operating pressure source 5, which is implemented as a displacement pump, reversely, i.e., in the direction opposite to that during the withdrawal of fluid.

While the invention has been illustrated and described in detail in the drawing and foregoing description, such illustration and description is to be considered as exemplary and not restrictive in character, it being understood that only exemplary embodiments have been shown and described and that all changes and modifications that come within the spirit of the invention are desired to protected.

What is claimed is:

1. A sampler for dispensing and cooling a sample of a fluid withdrawn at a sampling location, said sample of fluid to be stored at a selectable storage temperature, said fluid having an instantaneous sampling temperature greater than the storage temperature, said sampler comprising:
   a vessel assembly and a cooling assembly thermally coupled to said vessel assembly, said vessel assembly including a tubular intake vessel for conducting the withdrawn fluid and, said vessel assembly including a plurality of storage vessels for storing fluid samples to be dispensed in succession, one of said storage vessels adapted for storing said fluid sample withdrawn at said sampling location; and
   said cooling assembly including a first cooling volume being thermally coupled to said vessel assembly and being operable to cool the fluid samples to the storage temperature, and a second cooling volume being thermally coupled to said vessel assembly and being operable to cool the withdrawn fluid to a temperature below the sampling temperature wherein:
   said storage vessels are disposed in said first cooling volume, and at least a section of said vessel assembly is disposed in said second cooling volume.

2. A sampler as claimed in claim 1 wherein the second cooling volume is embedded in the first cooling volume.

3. A sampler as claimed in claim 1 wherein said vessel assembly further includes a metering vessel temporarily closable at an outlet end for metering the fluid sample.

4. A sampler as claimed in claim 1, wherein: said vessel assembly further includes a distributing vessel for dispensing the fluid sample, withdrawn at said sampling location into said one of said storage vessels adapted for storing said fluid sample.

5. A sampler as claimed in claim 4, wherein:
the second cooling volume includes a cooling element disposed at the distributing vessel for setting an internal temperature of the distributing vessel.

6. A sampler as claimed in claim 4, wherein:
said
said second cooling volume includes a cooling element disposed at the distributing vessel for setting an internal temperature of the distributing vessel.

7. A sampler as claimed in claim 1, wherein:
the second cooling volume is formed at least by a cooling element of the cooling assembly, said cooling element being disposed at said intake vessel for setting an internal temperature of said intake vessel.

8. A sampler as claimed in claim 7, wherein:
the cooling element is a flow cooler.

9. A sampler as claimed in claim 1, wherein:
the intake vessel is partially contacted by the first cooling volume.

10. A sampler as claimed in claim 1, wherein:
said vessel assembly and said cooling assembly are configured to dispense and cool, respectively, at least one of a drinking water and a wastewater.

11. The sampler as claimed in claim 1, further comprising:
a vacuum pump operable to reduce a static pressure within said vessel assembly.

12. A sampler as claimed in claim 1, further comprising:
a cabinet, at least a portion of said vessel assembly being disposed in said cabinet, wherein:
said first cooling volume is formed by a cool-storage room provided directly in said cabinet.

13. A sampler as claimed in claim 1 wherein:
the intake vessel is implemented, at least in sections, as a flexible tube.

14. A sampler as claimed in claim 1 wherein:
the intake vessel is a tube of elastic material.

15. A sampler as claimed in claim 1 wherein:
the intake vessel is made of polyethylene.

16. A sampler as claimed in claim 1 wherein:
the intake vessel is made of glass.

17. A sampler for dispensing and cooling a sample of a fluid withdrawn at a sampling location, said sample to be stored at a selectable storage temperature, said fluid having an instantaneous sampling temperature greater than the storage temperature, said sampler comprising:
   a vessel assembly and a cooling assembly thermally coupled to the vessel assembly, said vessel assembly including a tubular intake vessel for conducting the withdrawn fluid, a metering vessel for metering the fluid sample and a storage vessel for storing the fluid sample; and said cooling assembly including a first cooling volume being thermally coupled to the vessel assembly and being operable to cool the fluid sample to the storage temperature, and a second cooling volume being thermally coupled to the vessel assembly and being operable to cool the withdrawn fluid to a temperature below the sampling temperature;
   wherein:
   at least the storage vessel is disposed in said first cooling volume: and
   the second cooling volume includes a cooling element disposed at the metering vessel for setting an internal temperature of the metering vessel.

18. A sampler for dispensing and cooling a sample of a fluid withdrawn at a sampling location, said sample to be stored at a selectable storage temperature, said fluid having an instantaneous sampling temperature greater than the storage temperature, said sampler comprising:
a vessel assembly of a predetermined volume, said vessel assembly including a tubular intake vessel for conducting the withdrawn fluid, a metering vessel for metering the fluid sample and a storage vessel for storing the fluid sample; and a cooling assembly thermally coupled to the vessel assembly, said cooling assembly including a first cooling volume being thermally coupled to the vessel assembly and being operable to cool the fluid sample to the storage temperature, and a second cooling volume being thermally coupled to the vessel assembly and being operable to cool the withdrawn fluid to a temperature below the sampling temperature;
wherein at least the storage vessel is disposed in said first cooling volume; and
said storage vessel and the metering vessel are disposed within the first cooling volume.

19. A sampler for dispensing and cooling a sample of a fluid withdrawn at a sampling location, said sample to be stored at a selectable storage temperature, said fluid having an instantaneous sampling temperature greater than the storage temperature, said sampler comprising:
a vessel assembly including a tubular intake vessel for conducting the withdrawn fluid and a storage vessel for storing the fluid sample;
a displacement pump operable to generate fluid-conveying displacement motions of the intake vessel; and
a cooling assembly thermally coupled to the vessel assembly, said cooling assembly including a first cooling volume being thermally coupled to the vessel assembly and being operable to cool the fluid sample to the storage temperature, and a second cooling volume being thermally coupled to the vessel assembly and being operable to cool the withdrawn fluid to a temperature below the sampling temperature;
wherein at least the storage vessel is disposed in said first cooling volume, and wherein at least a section of the vessel assembly is disposed in said second cooling volume.

20. A sampler as claimed in claim 19, further comprising:
a plurality of storage vessels for storing fluid samples to be dispensed in succession.

21. A sampler as claimed in claim 19, wherein:
said storage vessels are disposed within said first cooling volume.

22. The method as claimed in claim 19, wherein:
the sampler comprises a plurality of storage vessels for storing fluid samples to be dispensed in succession, said plurality of storage vessels being disposed within a cabinet of said sampler.

23. The method as claimed in claim 22, wherein:
said plurality of storage vessels are disposed in said cabinet within said first cooling volume.

24. A method of dispensing and cooling a sample of a fluid withdrawn at a sampling location by means of a sampler, said sample to be stored at a storage temperature value, said fluid having a sampling temperature value greater than the storage temperature value, said sampler comprising:
a cabinet; and
a vessel assembly including a tubular intake vessel for conducting the withdrawn fluid; and a plurality of storage vessels for storing fluid samples to be dispensed in succession, one of said storage vessels adapted for storing said fluid sample withdrawn at said sampling location, and said vessel assembly having an internal temperature, wherein prior to the dispensing said internal temperature of the vessel assembly having an initial internal temperature value being lower than the sampling temperature value; and said sampler further comprising a cooling assembly thermally coupled to the vessel assembly for adjusting said internal temperature of the vessel assembly, said cooling assembly comprising at least a first cooling volume having a cooling temperature, said first cooling volume being disposed within said cabinet and said plurality of storage vessels being disposed in said cabinet within said first cooling volume, and said cooling temperature of said first cooling volume being set at the storage temperature value at least after the storing of said sample, said method comprising steps of:
lowering the internal temperature of the vessel assembly by means of the cooling assembly to a temperature value lower than the initial internal temperature value of the vessel assembly;
during or after the step of lowering the internal temperature of the vessel assembly, letting the withdrawn fluid flow through said intake vessel; and
transferring a partial volume of the withdrawn fluid from said intake vessel to said storage vessel to obtain the fluid sample, wherein:
said step of lowering the internal temperature of the vessel assembly includes a step of lowering said cooling temperature of said first cooling volume to a temperature value lower than said storage temperature value.

25. A method as claimed in claim 24, wherein:
the fluid sample is withdrawn from an aqueous fluid.

26. The method as claimed in claim 24 further comprising a step of:
letting a part of said withdrawn fluid flow back through said intake vessel.

27. The method as claimed in claim 24, further comprising a step of:
letting a part of said withdrawn fluid flow back to said sampling location.

28. The method as claimed in claim 24, further comprising a step of:
setting a section of the intake vessel into fluid-conveying displacement motions.

29. The method as claimed in claim 24, further comprising the steps of:
reducing a static pressure in the volume of said vessel assembly; and increasing the static pressure in a volume of said vessel assembly.

30. The method as claimed in claim 24, further comprising the step of:
using a pump to reduce a static pressure within said vessel assembly.

31. The method as claimed in claim 24, wherein:
the first cooling volume is formed by a cool-storage room provided directly in said cabinet.

32. The method as claimed in claim 24, wherein:
the intake vessel is implemented, at least in sections, as a flexible tube.

33. The method as claimed in claim 24 wherein:
the intake vessel is a tube of elastic material.

34. The method as claimed in claim 24 wherein:
the intake vessel is made of polyethylene.

35. The method as claimed in claim 24 wherein:
the intake vessel is made of glass.

* * * * *